United States Patent
Brais

[19]

[11] Patent Number: 5,833,740
[45] Date of Patent: Nov. 10, 1998

[54] AIR PURIFIER

[76] Inventor: Normand Brais, 209, Des Tilleuls, Rosemère, Québec, Canada, J7A 4K6

[21] Appl. No.: 756,253

[22] Filed: Nov. 25, 1996

[51] Int. Cl.$^6$ ................................ B03C 3/00; B03C 3/38
[52] U.S. Cl. .................... 96/16; 96/62; 96/63; 96/18; 55/279; 422/24
[58] Field of Search .......................... 422/121, 186.04, 422/906, 24; 96/16, 139, 62, 63, 18; 55/279, DIG. 30

[56] References Cited

U.S. PATENT DOCUMENTS

| | | | |
|---|---|---|---|
| 3,653,185 | 4/1972 | Scott et al. | 55/220 |
| 3,750,370 | 8/1973 | Brauss et al. | 55/279 |
| 4,990,313 | 2/1991 | Pacosz | 422/121 |
| 5,112,370 | 5/1992 | Gazzano | 55/279 |
| 5,160,513 | 11/1992 | Koves | 55/320 |
| 5,330,722 | 7/1994 | Pick et al. | 422/121 |
| 5,334,347 | 8/1994 | Hollander | 422/24 |
| 5,492,557 | 2/1996 | Vanella | 96/16 |

*Primary Examiner*—Ponnathapura Achutamurthy
*Assistant Examiner*—P. Ponnaluri
*Attorney, Agent, or Firm*—Goudreau Gage Dubuc & Martineau Walker

[57] ABSTRACT

Disclosed is a chemical and biological air purifier. The air purifier has a housing having an inlet and an outlet both aligned on a longitudinal axis, a turbulence generator, one or more vacuum ultraviolet (UV) sources achieving a chemical purification and one or more germicidal ultraviolet (UV) sources achieving the biological purification. The turbulence generator is mounted within the housing downstream of the inlet and promotes a dispersion and mixing of air received through the inlet. The vacuum UV source is mounted within the housing downstream of the turbulence generator and breaks oxygen molecules into mono-atomic oxygen which then reacts with chemical contaminants present in the air and degrades them by successive oxidation to odorless and inoffensive byproducts. The turbulence generator reduces the production of ozone by increasing the contact between the mono-atomic oxygen and the chemical contaminants. The germicidal UV-C source is mounted within the housing parallel to the longitudinal axis of the housing downstream of the vacuum UV source. The germicidal UV-C source, in use, kills biological contaminants present in the air by irradiation and degrades residual ozone produced by the vacuum UV sources into molecular oxygen, thereby purifying air from the biological contaminants and residual ozone.

27 Claims, 7 Drawing Sheets

AIR PURIFIER

FIELD OF THE INVENTION

The present invention relates to an air purifier used to purify air from chemical and biological air contaminants.

BACKGROUND OF THE INVENTION

Indoor air quality problems, often referred to as "Sick Building Syndrome" costs North America well over 100 Billion dollars each year in health care, absenteeism, lost production time and lost revenue.

Studies have demonstrated that the air inside businesses and homes can be more contaminated than the outside air of some industrialized cities.

Contaminants have generally been classified into two categories: chemical contaminants and biological contaminants.

CHEMICAL CONTAMINANTS

Most chemical contaminants found in buildings arise from the increasing use of synthetic materials such as pressed wood, nylon carpets, plastics, solvents and other household maintenance products.

The characteristics of a few common chemical contaminants and their effects on health are summarized in table 1, which is derived from the American Conference of Governmental Industrial Hygienists (ACGIH 1989).

TABLE 1

| Chemical contaminant | Health effects | Major indoor sources |
| --- | --- | --- |
| Formaldehyde | Nausea, eye irritation, headaches, confusion | Furniture, carpets, synthetic panels, plywood, press wood, insulation |
| Carbon monoxide | Headaches, nausea, fatigue | Cigarette, cooking smoke |
| Benzene | Nausea, nose irritation, headaches | Paint, synthetic materials, printing inks |
| Toluene | Nausea, nose irritation, headaches | Paint, solvents, nail polish |
| Hydrocarbons (VOC) | Nausea, headaches | Oils, fuels, greases, fireplace, cigarette |
| Aerosols | Eye irritation, nausea, headaches | Hair spray, deodorants |

BIOLOGICAL CONTAMINANTS

Microorganisms represent the major source of biological contaminants. Viruses, bacteria, fungi and protozoa, as well as their by-products, such as antigens, mycotoxins and bacterial endotoxins are commonly found in buildings or workplaces.

The characteristics of a few common biological contaminants, their effects on health as well as their major indoor source are summarized in table 2.

TABLE 2

| Biological contaminants | Health effects | Major indoor sources |
| --- | --- | --- |
| Bacteria | Pneumonia, fever, hypersensitivity, asthma, pneumonitis | Water reservoir, hot water, hot surface, humidifier |
| Fungi, fungal spores | Asthma, rhinitis, mycosis, mycotoxicosis | Outdoor air, spores, animals, plant, damp surface |
| Protozoa | Infections | Water reservoir, humidifier |
| Viruses | Infections | Water reservoir, humidifier |
| Algae | Asthma, Rhinitis | Outdoor air |
| Pollen | Asthma, Rhinitis, hypersensitivity | Outdoor air, green plants |
| Arthropods, antigens | Asthma, Rhinitis | Carpet, feces, mattress, dust, animals |
| Antigens from mammals | Asthma, Rhinitis, Hypersensitivity | animal hair, skin scale, saliva |

Most environments contain a large variety of bacteria. It is generally acknowledged that health risks increase only with the increase of pathogen bacteria concentration in an indoor environment. Another increase of health risks occurs when the pathogen bacteria or their by-products are suspended and successfully air-borne towards the breathing zone of the indoor environment. Legionnaire's disease, some pneumonia and tuberculosis are infectious diseases caused by airborne bacteria. Bacteria can also cause hypersensitivity pneumonitis such as humidifier fever. Except in the case where a building exhibits serious water leaks, the main source of bacteria in a building comes from human occupation. Bacteria concentration of 1000 $CFU/m^3$ (Colony Forming Unit per cubic meter) in houses and up to 20,000 $CFU/m^3$ in kindergartens have been reported.

Endotoxins are structural components of a bacteria cell wall. More precisely, they are lipopolysaccharides produced by gram-negative bacteria that are released after bacterial death. Dangerous levels of airborne endotoxins have been reported in numerous work environments, including offices and laboratories. They can cause fever and malaise, changes in white blood cell counts, and respiratory and gastrointestinal problems.

Fungi exist in over 100 000 known species. Microscopic fungi include yeasts and molds. Most fungi produce spores (structures whose role is propagation) that are carried by the air. The diameter of these spores varies from approximately 1 to 60 microns ($10^{-6}$ meters). Most substances containing carbon, abundant in indoor and outdoor environments, can serve as nutrients for molds. Accumulation of humidity in the indoor environment is the most important factor to be controlled to limit fungal growth.

Some fungi can invade individuals and cause infectious diseases. However, several molds produce proteins or glycoproteins that are highly antigenic i.e. capable of triggering an immune response and can cause, as reactions, hypersensitivity diseases or allergies in susceptible individuals. These allergy reactions include rhinitis, allergic asthma and extrinsic allergic alveolitis. Growing molds may also produce several volatile organic compounds. These volatile compounds cause the characteristic moldy odour, among other things.

Protozoa are microscopic, single cell organisms. There are thousands of species of protozoa varying in size, structure, morphology and physiologic characteristics, most of them harmless. Some are used in biotechnology and others are capable of causing diseases in plants and animals. These organisms are found in humidifiers and air filters, water treatment plants, thermal effluents, cooling systems, etc. A study has shown that humidifier fever in office workers was probably caused by antigens from Naegleria aerosolized by a humidifier (American Conference of Governmental Industrial Hygienists ACGIH, (1989)).

Viruses vary in size from 20 to 400 nm. Airborne viruses are generally transmitted from person to person by droplets or projection such as sneezing or coughing.

Antigens are organic substances capable of triggering an immune response In humans. Practically all living organisms contain proteins, glycoproteins or polysaccharides with antigenic potential. This is a reason why several microorganisms (bacteria, fungi, protozoa, acarids, etc.) have an impact on health via the action of antigens on the immune system. Of all the hypersensitivity diseases, only hypersensitivity pneumonitis, allergic asthma, allergic rhinitis and allergic aspergillosis are known as being a result of exposure to airborne antigens. The cause-effect relationship for microbial allergens is well known, but the complete characterization of the dose-response relationship is not.

Water reservoirs are good growth media for some bacteria, fungi and protozoa. Consequently, ventilation system components, particularly some types of humidifiers, can aerosolize droplets from water reservoirs and therefore are of special interest due to the production of small antigenic particles (smaller than 2–3 microns). Epidemics of hypersensitivity pneumonitis have occurred in individuals when building humidification systems were contaminated.

In residences, the most important sources of antigens relating to human health are mites, cats, cockroaches, and molds. All these organisms carry antigens, which can cause allergic asthma and allergic rhinitis. Dust mites (acarids) and their droppings that have accumulated in bedding, furniture or in places where the relative humidity and temperature are favourable, also produce antigens.

INDOOR AIR QUALITY PROBLEM

It is now of common knowledge that the energy efficient designs of the 1970's resulted in tighter building envelopes with improved insulation and low energy consuming ventilation, without operable windows. Under these conditions, indoor pollutants are not sufficiently diluted with fresh air. Furthermore, the number of indoor air pollutant sources generally increases over the years. Indeed, new building materials, products and furnishing emit a significant number of potentially hazardous chemicals into the air. The resulting situation is an increase in contaminants circulating through the indoor environment, with insufficient outside air introduced to dilute the contaminants.

Indoor air quality (IAQ) is a complex issue, much more so than any single environmental issue. There are hundreds of pollutants that affect IAQ and thousands of sources of these pollutants. Research indicates that more than 900 different contaminants are present in conventional indoor environments.

If need for comfort, health and well being are not satisfied, building users may begin to complain of symptoms which are associated with poor IAQ.

Headaches, burning and itching eyes, respiratory difficulties, skin irritation, nausea, congestion, cough, sneezing and fatigue are some of the most common complaints. Another complaint associated with poor IAQ is that there is an unidentifiable smell in the indoor environment. Odours are often associated with a perception of poor air quality.

An increasing percentage of the human population is becoming more sensitive to a number of chemicals in indoor air, which are often at very low concentrations. This condition, which has been identified as Multiple Chemical Sensitivity (MCS), is currently the object of medical research.

According to the United States Environmental Protection Agency (EPA), the effects of indoor IAQ problems are often non-specific symptoms rather than clearly defined illnesses. Although they can be vague, the symptoms seem generally worse after a day in the workplace and may altogether disappear when the occupant leaves the building.

Legionnaire's disease, tuberculosis and hypersensitivity pneumonitis are examples of building related illnesses that can have serious and even life-threatening consequences.

In light of the above, the need for efficient air purification is easily understandable.

BRIEF DESCRIPTION OF THE PRIOR ART

The simplest and most common way of maintaining reasonable air quality standards inside a building is to dilute the indoor air with outdoor air through an adequate ventilation system. Not only is this method energy intensive but the indoor air quality will be satisfactory only if the outside air is not itself contaminated. Experiments have demonstrated that by continuously changing a portion of the air inside a conventional house with fresh air from outside, it is possible to maintain a level of 1000 $CFU/m^3$ inside the house if the air outside has a level of 500 $CFU/m^3$.

In order to purify air from essentially solid particulate contaminants, such as dust, air purifiers using various types of air filters are conventionally used. Of course, when air filters are used in buildings, they require routine maintenance to maintain them at an optimal efficiency level. Filter based air purifiers can be classified as passive air purification devices. When filters become clogged, ventilation air flow drop down, which further aggravates the IAQ problem.

One major drawback of the filter based air purifiers is that they become a source of new pollutants if they are not regularly cleaned. Indeed, bacterial growth on the filter is favoured by the concentration of organic dust and moisture. Most bacteria and viruses are too small to be captured by filters, except for very fine filters, that exhibit relatively high pressure drop for low air flows.

To overcome this drawback, U.S. Pat. No. 5,330,722, issued to William PICK et al. on Jul. 19, 1994, suggest the use of an ultraviolet (UV) lamp to irradiate the filter of an air purifier to thereby expose the filter to germicidal levels of radiation and therefore rendering the air purifier consistently effective.

Another solution of the above detailed drawback is described in U.S. Pat. No. 3,750.370, issued to Erhard BRAUSS et al. on Aug. 7, 1973. In this document, Brauss proposes the use of germicidal UV lamps in order to control biological contaminants by irradiating them while they are in suspension in the air to be treated.

Although these methods may be effective for some biological contaminants, they are inoperant for molecular size non-living contaminants such as formaldehyde, carbon monoxide, and other commonly found indoor chemical compounds.

Three general methods are currently used to purify indoor air and to render molecular size contaminants harmless.

The first method consists in adsorbing the contaminants on an activated carbon or potassium permanganate filters. A major drawback with this method is the required frequent replacement of the filter. This method is therefore a high maintenance and expensive solution which is not well adapted for residential use. Furthermore, should this method gain general acceptance and thereby large scale commercialization, the disposal of a large quantity of contaminant saturated filters would create a new problem.

The second method consists in the direct incineration of the contaminants by way of flame. Major drawbacks of this method are the high costs involved in the operation of a contaminant incinerator and the fact that the treated air cannot be recycled and must be exhausted. This method is therefore not suited for low contaminant concentrations or small scale applications.

The third method involves oxidation by ozonation of the contaminants to render them harmless by contact with oxygen molecules. Indeed, the meta-stable molecule of ozone, which is formed of three oxygen atoms, is used as an oxidizer to degrade chemical compounds. This method is highly efficient and devices using this method have been used for a number of years for rapid decontamination and elimination of smoke odours in an environment that has undergone a fire. However, the levels of ozone production of these devices are dangerously high during the treatment of the room and must therefore be used only in unoccupied spaces.

More specifically, the Occupational Safety and Health Association (OSHA) specifies, in its standard to be complied with, that the maximum ozone concentration in the air of an occupied room is 0.05 ppm (parts per million).

As will be apparent to one of ordinary skill in the art, in order to be efficient, an ozone generation based air purifier needs to produce ozone concentration levels that are several times the maximum-level of the OSHA standard.

OBJECTS OF THE INVENTION

An object of the present invention is therefore to provide an improved air purifier.

Another object of the invention is to provide an air purifier that simultaneously performs chemical and biological purification by ozone production while avoiding the drawbacks of the prior art.

SUMMARY OF THE INVENTION

More specifically, in accordance with the present invention, there is provided an air purifier comprising:

a housing having an air inlet for receiving air and an air outlet for exhausting air, means mounted within the housing for generating monoatomic oxygen downstream of the air inlet, the generated mono-atomic oxygen reacting with chemical contaminants present in the air and degrading the contaminants by successive oxidation to odorless and inoffensive by-products, thereby purifying air from the chemical contaminants; a portion of the mono-atomic oxygen generated combining with oxygen molecules present in the air to form residual ozone; and means mounted within the housing for generating low frequency photons downstream of the mono-atomic oxygen generating means, the low frequency photons killing by irradiation biological contaminants present in the air and degrading the residual ozone produced, thereby purifying air from the biological contaminants and from residual ozone.

In a preferred embodiment of the present invention, an internal surface of the housing is made of UV reflective material such as aluminum.

In another preferred embodiment, the air purifier includes a turbulence generator including a plurality of deflective baffles extending essentially perpendicular to the air inlet and oriented in such a manner as to generate turbulence and swirl in the air entering in the housing through the air inlet promoting dispersion and mixing of air received within the housing through the air inlet.

In yet another preferred embodiment, the vacuum UV source includes a UV lamp tube emitting energetic UV photons having a wavelength in a range of about 170 to about 220 nanometers, and the low frequency photon generating means includes a germicidal UV-C lamp tube emitting UV-C photons having a wavelength in a range of about 220 to about 288 nanometers.

In another embodiment of the present invention, the UV lamp tube emitting energetic photons and the germicidal UV-C lamp tube are embodied together in a ballasted dual zone mercury vapor lamp.

The air purifier according to the present invention presents many advantages. For example, it allows for the destruction of more than 80%, preferably more than 99%, of the organisms in the treated area, lowers the CFU count in a room to the same degree as would be obtained by ventilating the room at a rate of more than 100 air changes per hour.

Other objects, advantages and features of the present invention will become more apparent upon reading of the following non restrictive description of preferred embodiments thereof, given by way of example only with reference to the accompanying drawings.

DESCRIPTION OF THE PREFERRED EMBODIMENT

For the purpose of simplicity, the same numeral references have been used throughout the description and drawings to identify the same structural elements.

Figure 1:
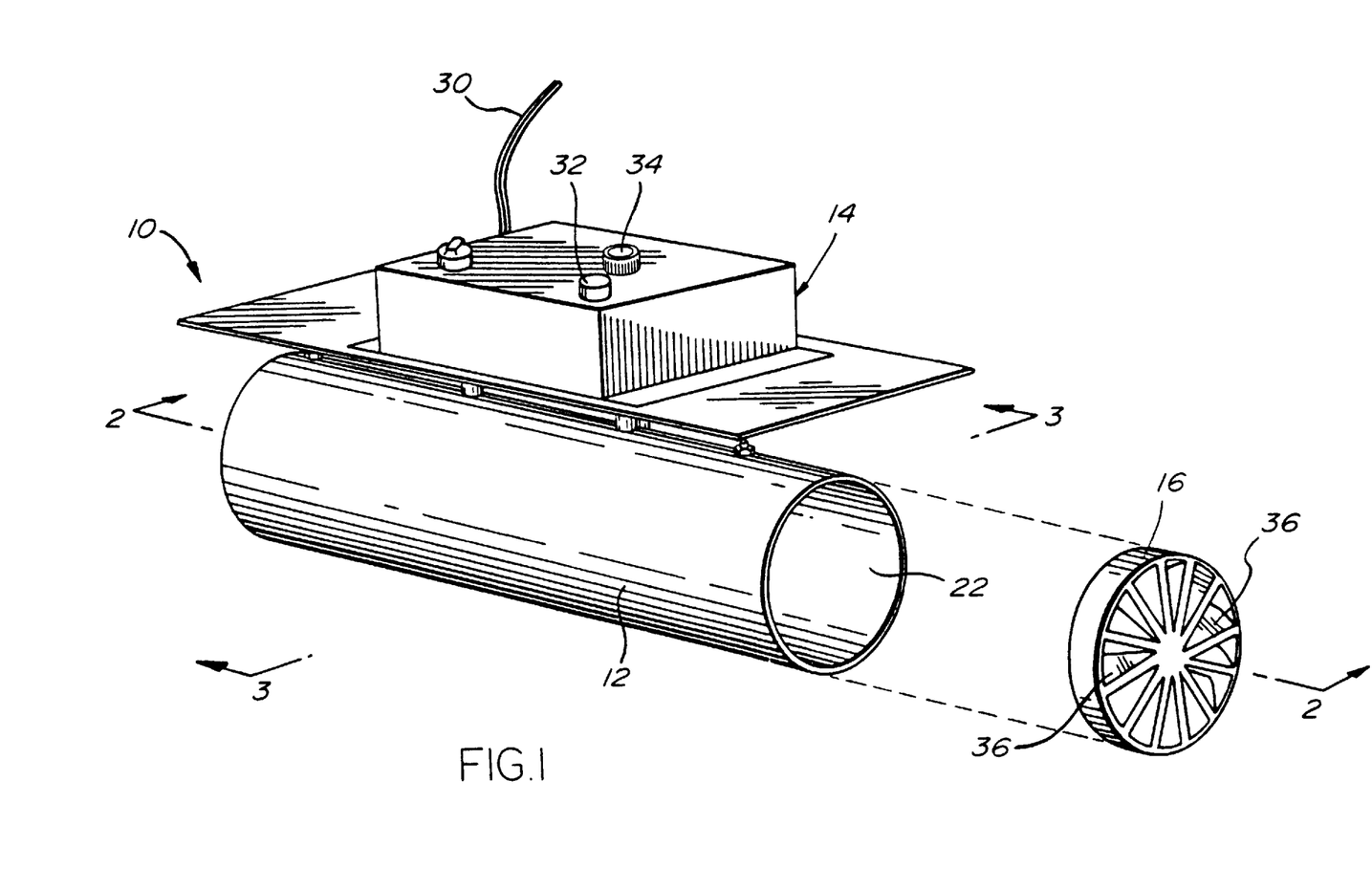
FIG. 1 is a perspective view of a chemical and biological air purifier according to a first embodiment of the present invention.
Figure 2:
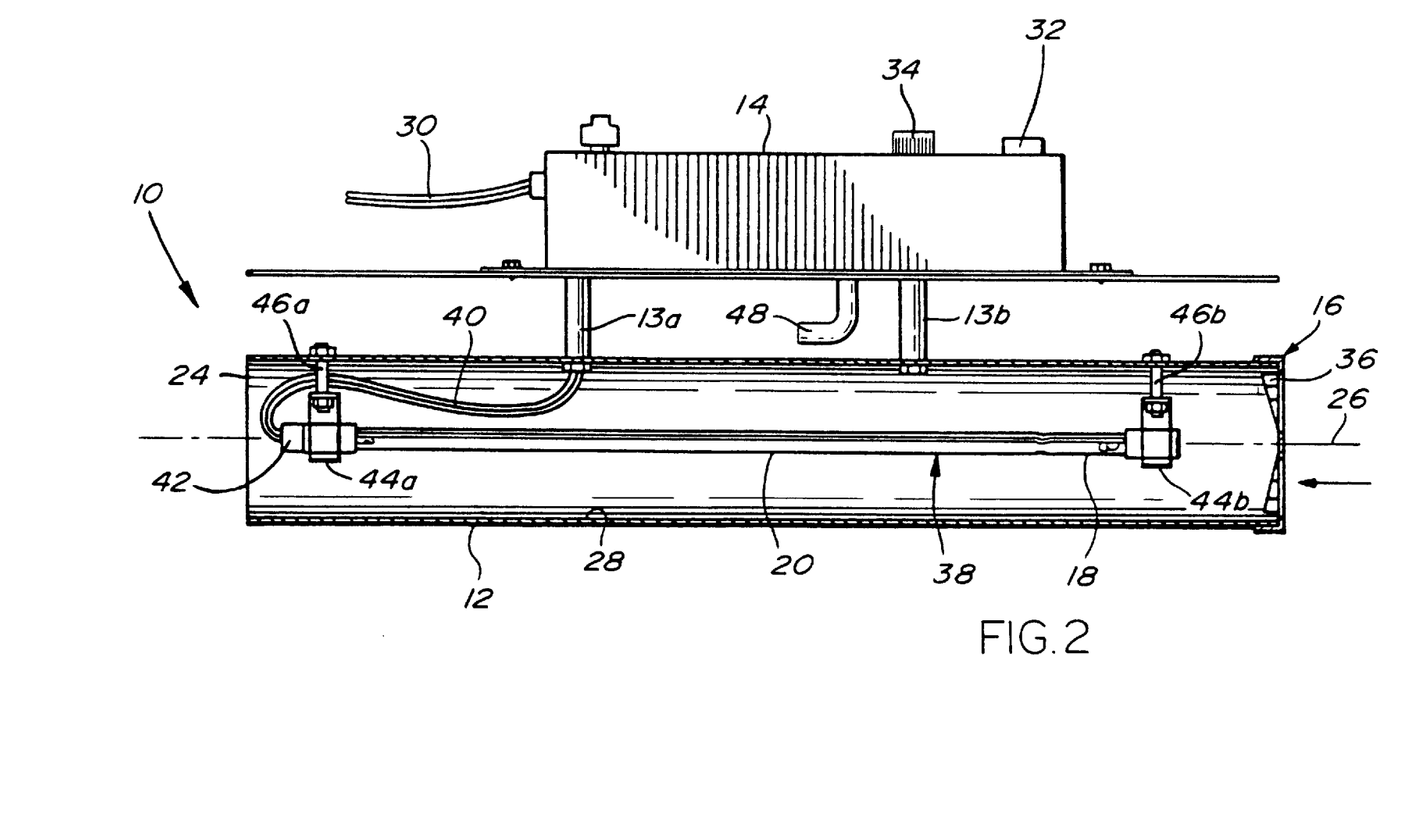
FIG. 2 is a longitudinal cross-sectional view taken along line 2—2 of FIG. 1.
Figure 3:
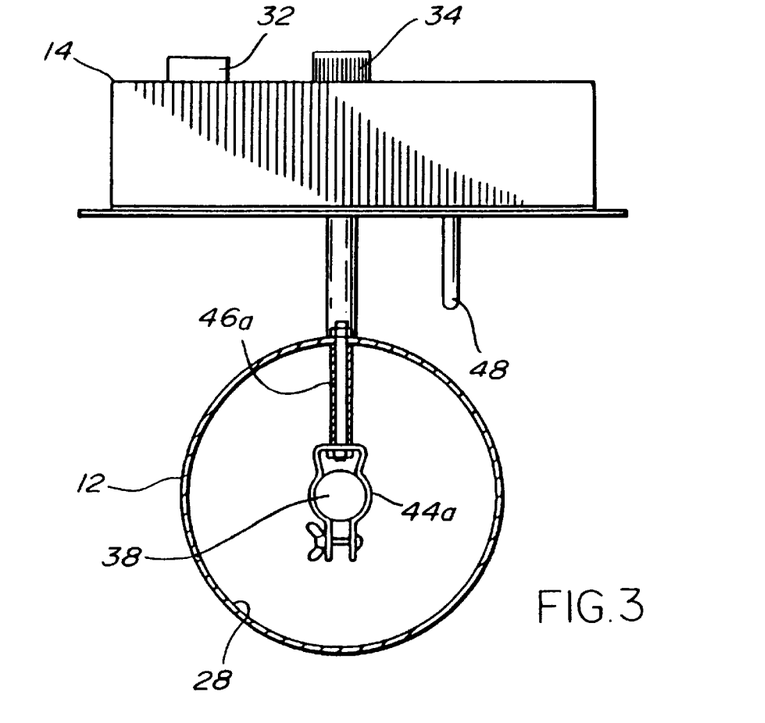
FIG. 3 is a transversal cross-sectional view taken along line 3—3 of FIG. 1.

FIGS. 1 to 3 of the appended drawings illustrate a chemical and biological air purifier 10 according to a first embodiment of the present invention. The air purifier 10 includes a housing 12, a control box 14 mounted to the housing 12 through posts 13a and 13b, a turbulence generator 16, a mono-atomic oxygen generator under the form of a vacuum UV source 18 and a low frequency photons (UV-C photons) generator under the form of a germicidal UV-C source 20.

The housing 12 has an inlet 22 and an outlet 24, both aligned on a longitudinal axis 26, and a reflective inner surface 28 to reflect back photons emitted from the germicidal UV-C source 20. It has been found that a reflective inner surface made of aluminum is efficient to reflect UV photons. Of course, other reflective materials may be used.

The control box 14 includes an electrical wire 30, a ballast (not shown) and a switch 32 to activate or deactivate both the vacuum UV source 18 and the germicidal UV-C source 20, and a view port 34. Many types of ballasts may be used depending on the type of UV sources 18 and 20 used. These ballasts are well known to one skilled in the art. It has been found that ballasts sold by ROBERTSON TRANSFORMER CO. under the part number ss2060-4p, ss16550 p, seghp287 p are adequate. The view port 34 is aligned with post 13b to enable visual confirmation of the operation of the UV sources 18 and 20. Of course, the post 13b is hollow and the view port 34 is provided with adequate filters (not shown) to prevent eye damage.

In FIGS. 1 to 3, the control box 14 has been shown mounted to the housing 12 through the posts 13a–13b. However, the control box 14 could be remotely located if such is desired. Of course, if such is the case, the view port 34 is to be modified or eliminated.

The turbulence generator 16 is mounted at, or downstream of, the air inlet 22 and includes deflective baffles 36 oriented in such a manner as to generate turbulence in the air entering the housing 12 through the air inlet 22. The possible orientations of the baffles 36 to generate air turbulence are believed well known in the art and will not be discussed further herein.

The vacuum UV source 18 is embodied together with the germicidal UV-C source 20 into a single ballasted dual zone mercury vapor lamp 38 comprising an upstream portion (see 18), acting as the vacuum UV source and emitting photons in a wavelength range varying from 170 to 220 nm (nanometers or $10^{-9}$ meters) and a downstream portion (see 20), acting as the germicidal UV-C source and emitting photons in another wavelength range varying from 220 to 288 nm. It has been found that a mercury vapor lamp sold by LIGHT SOURCES INC.(Milford, Conn.) under the part number GPH457T5VH/L4P operates properly for the present purpose.

One advantage of using a dual zone lamp embodying the vacuum UV source and the germicidal UV-C source is the fact that both sources will stop simultaneously should one source be faulty. The risk of emitting large amount of ozone is therefore eliminated.

It is to be understood that more than one ballasted dual zone mercury vapor lamp 38 may be used.

It is also to be noted that the dual zone mercury vapor lamp 38 could have any shape as long as the vacuum UV source 18 is upstream of the germicidal UV-C source 20.

Figure 6:
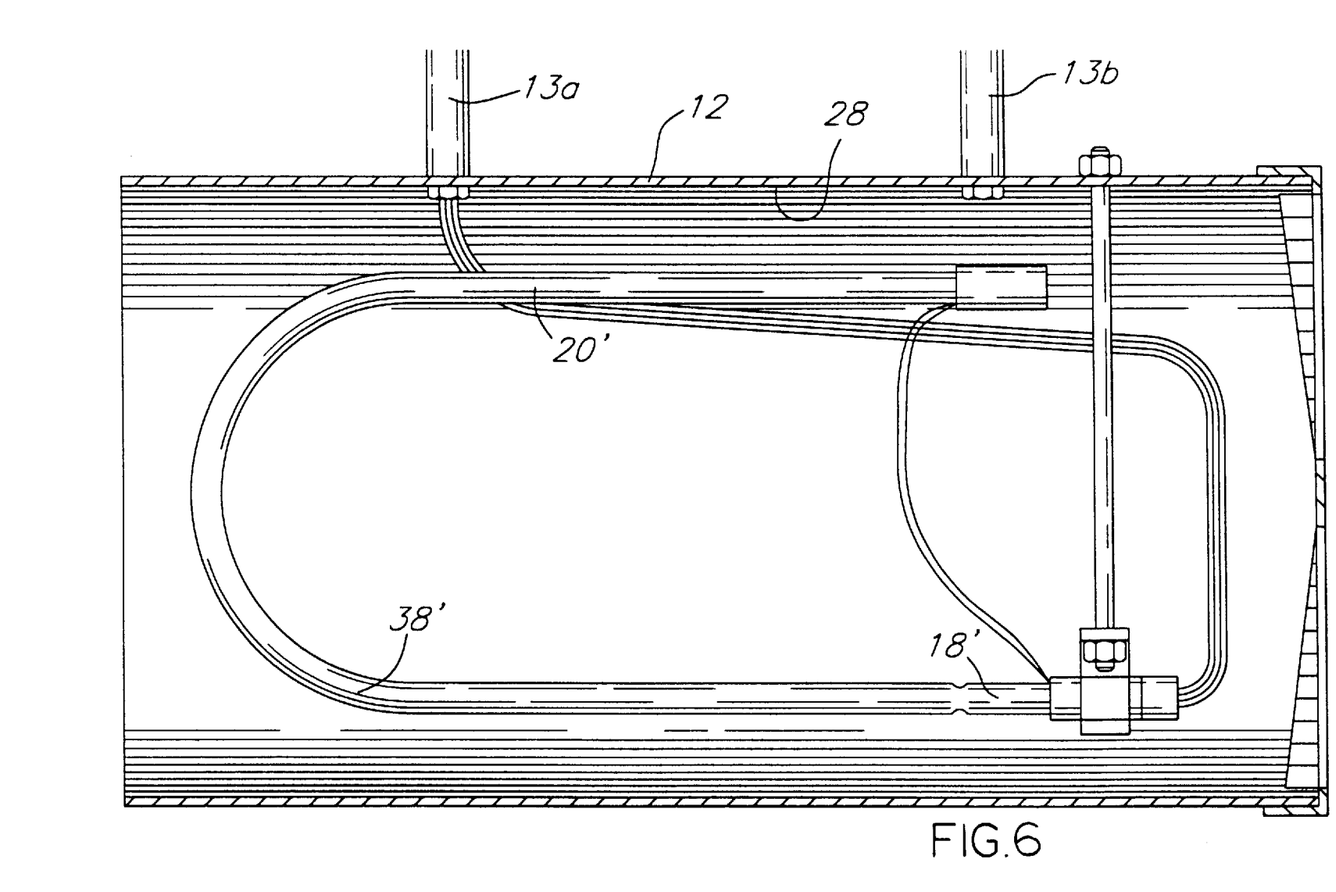
FIG. 6 is a longitudinal cross-sectional view similar to the one of FIG. 2, illustrating an air purifier according to a third embodiment of the present invention.

Accordingly, FIG. 6 of the appended drawings illustrates another embodiment of the present invention where the dual zone mercury vapor lamp is a J-shaped dual zone mercury vapor lamp 38' comprising a straight upstream portion 18' acting as the vacuum UV source and a U-shaped downstream portion 20' acting as the germicidal UV-C source. The J-shaped dual zone mercury vapor lamp 38', in use, accomplishes a better purification than the straight dual zone mercury vapor lamp 38 of FIGS. 1–3 and is more compact than the straight dual zone mercury vapor lamp 38, thereby reducing the overall size of the housing 12 and thus the size of the air purifier 10. Indeed, it has been calculated that, for bacteria having a lethal dose of 10,000 erg/cm$^2$, the killing efficiency is increased by about 6% while it is increased by about 17% for bacteria having a lethal dose of 100,000 erg/cm$^2$. These efficiency increases arise from the fact that the mean distance between any point in the housing and the J-tube is decreased, therefore increasing the mean exposure level. Similarly, the use of an housing having an elliptical cross-sectional profile (not shown) would increase the killing efficiency by about 1.4% for the same reasons described above.

Returning to FIGS. 1–3, the dual zone mercury vapor lamp tube 38 is connected to the ballast via electrical wiring 40 and socket 42. The dual zone mercury vapor lamp tube 38 is mounted to the housing 12 through clamps 44a, 44b and supports 46a, 46b.

A probe 48, connected to a vacuum switch (not shown), for example, the one sold by MICROPNEUMATIC LOGIC (Ft. Lauderdale Fla.), can also be mounted inside the housing 12 for detecting air circulation. The probe 48 detects differences of air pressure between the inside and the outside of the housing 12 and upon detecting such differences of pressure, sends a signal to the vacuum switch to activate or deactivate the dual zone mercury vapor lamp tube 38.

It is worth mentioning that the housing 12 of the air purifier 10 could be replaced by a film, adhesive on one side and photon reflective on another side, with which an inner portion of a ventilation duct could be wallpapered (not shown). Then, the electrical wiring 40 and the probe 48 would have to be inserted through the ventilation duct. The electrical wires 40 would only need to be connected to the dual zone mercury vapor lamp 38 which would be inserted in the duct and mounted therein.

The photons emitted from the vacuum UV source 18 are efficient to produce mono-atomic oxygen at the proximity of the surface of that UV source 18. The turbulence generator 16 contributes to diffuse the mono-atomic oxygen formed on the surface of the vacuum UV source 18, increasing the probability of an "encounter" between the mono-atomic oxygen and a chemical contaminant, present in the air introduced in the housing 12 and react with this contaminant. If it is not the case the mono-atomic oxygen will react with an oxygen molecule to produce an ozone molecule. Thereby the chemical purification efficiency is increased and the production of residual ozone from the reaction between mono-atomic oxygen with molecular oxygen is decreased. Accordingly, it is greatly advantageous to generate turbulence in the air entering the housing 12.

As will be apparent to one of ordinary skill in the art, the turbulence generator 16 could be replaced by other devices for causing turbulence, for example, by a motor-driven fan to cause turbulence in the air in the vicinity of the vacuum UV source 18.

The operation of the air purifier 10 will now be described. Upon activation of the switch 32, the air purifier 10 enters a standby mode and waits for a signal from the probe 48 detecting air circulation. Upon circulation detection, the probe 48 signals to the vacuum switch that air is circulating in the proximity of the housing which then activates the ballasted dual zone mercury vapor lamp 38.

The air entering the housing 12 through the air inlet 22 is transformed in a turbulent flow by the turbulence generator 16. This turbulent flow of air increases the diffusion rate of the mono-atomic oxygen generated by the vacuum UV source 18 near its surface. The oxidation of chemical contaminants is almost instantaneous.

Excess mono-atomic oxygen can produce ozone, which is a harmful gas, as a by-product of this process. Indeed, the combination of mono-atomic oxygen with molecular oxygen produces ozone.

However, the germicidal UV-C source 20 of lower frequency, produces UV-C photons, preferably of a wavelength of 254 nm, with a proper specific energy (about 27 kJ/mol) to decompose this residual ozone into regular molecular oxygen. The UV-C photons emitted, producing UV radiation, are confined by the reflective inner surface 28 of the housing 12 instead of being absorbed and lost. Preferably, the reflective inner surface 28 has a coefficient of reflection of at least 60% for UV-C wavelengths. The reflection of the photons ensures a high efficiency or quantum yield of the UV-C photons. The UV-C photons are emitted by a UV-C zone which is also a powerful germicide that kills living cells such as fungi, viruses and spores by irradiation. Accordingly, the biological contaminants receive a lethal dose of UV-C radiation, that inhibits their reproduction by modifying their DNA.

At a reaction level, at least three steps take place: a first activation phase, a reaction phase and a neutralization and germicidal phase.

The activation phase is characterized by the production of mono-atomic oxygen. Energetic UV photons emitted from the high intensity UV source 18, preferably in the wavelength range from 170 to 220 nm, break down some oxygen molecules into activated mono-atomic oxygen. The quantum yield, or the efficiency of this action is a function of the wavelength and intensity of the UV source. For example, a vacuum UV source of about 8 $\mu$W/cm$^2$ at 1 m has been found adequate.

The reaction phase is characterized by the oxidation of chemical contaminants. Activated mono-atomic oxygen are mixed with the air stream to be treated and reacts with chemical compounds contained therein, degrading it by successive oxidation to odorless and inoffensive by-products. If chemical contaminants are outnumbered by the activated mono-atomic oxygen, ozone will be formed as a by-product, which is a consequence of the further oxidization of regular molecular oxygen.

The neutralization and germicidal phase is characterized by the degradation of residual ozone formed and by the biological purification of the air. The lower intensity UV photons emitted by the germicidal UV-C source 20, preferably in the wavelength range from 220 to 288 nm, are used to neutralize the excess ozone generated in the reaction phase, by decomposing the excess ozone into regular molecular oxygen. A UV wavelength of 254 nm is preferred for the neutralization and germicidal phase. The 254 nm wavelength is well known in the art for its very high germicidal performance. In fact, the germicidal effect of sunlight was first discovered in England in 1877 by Downes and Blunt. Since their pioneer work, the effect of UV radiation on bacteria has been studied in detail and the relation between lethal action and wavelength is well known. The relationship between the germicidal effect and wavelength has a maximum effectiveness around 260 nm. and falls to a minimum at 320 nm. In a general way, this relationship is similar to the absorption curve for a nucleic acid (DNA) which is the basis of living organisms. Within the limits of experimental accuracy, the lethal action appears to be independent of the nature of bacteria to be killed. A UV-C source of about 70 $\mu$W/cm$^2$ at 1 m has been found adequate for this purpose.

Since 90% of the energy spectrum emitted by the germicidal UV-C source is concentrated at 253.7 nm by the use of the low pressure mercury vapor lamp, the germicidal relative effectiveness is close to 100%.

When bacteria are subjected to any lethal agent such as heat, disinfectants, x-rays or ultraviolet, they do not all die at once. A constant fraction of the bacteria present die with each increment of time. A fraction of the bacteria initially present which survives at any given time is called a survival ratio. A fraction killed is 1 minus the survival ratio. Quantities are expressed as a percent by multiplying by 100.

The killing rate is an exponential function of the time of exposure and the intensity of the ultraviolet radiation according to the equation:

$$\text{Kill Rate} = 1 - \frac{N}{N_0} = 1 - e^{-kIt}$$

Where $N_o$ is the number of bacteria initially present, N is the number of bacteria surviving at a time t of exposure to the ultraviolet photons, k is a lethal dose related constant depending upon the nature of the organism and I is the radiation intensity.

The radiation dose, defined as the product of I by t, required for (k×I×t) to equal 1 has been defined as a "lethe" and corresponds to a kill rate of 63.2%. A given dose results in a given survival ratio, regardless of whether the exposure consists of low intensity for a long time, or high intensity for a corresponding shorter time.

The temperature has little, if any, effect on the germicidal performance of UV radiation between 5 degrees and 37 degrees Celsius.

Different germicidal UV doses required for 90% killing rate of different biological contaminants are listed in table 3.

TABLE 3

| Biological contaminant | Energy required Ergs/cm$^2$ |
|---|---|
| Bacillus anthracis | 45200 |
| B. megatherium sp. (veg.) | 44400 |
| B. megatherium sp. (spores) | 27300 |
| B. paratyphosus (avererage of 3 strains) | 32000 |
| B. subtilis (mixed) | 71000 |
| B. subtilis (spores) | 120000 |
| Corynebacterium diphtheriae | 33700 |
| Dysentery facilli (average of 5 strains) | 22000 |
| Eberthella typhosa | 21400 |
| Escherichia coli | 30000 |
| Micrococcus candidus | 60500 |
| M. piltonensis | 81000 |
| Neisseria catarrhalis | 44000 |
| Phytomonas tumefaciens | 44000 |
| Proteus vulgaris | 26400 |
| Pseudomonas aerugenosa | 55000 |
| Ps. fluorescens | 35000 |
| Salmonella enteritidis | 40000 |
| S. typhimurium (average of 3 strains) | 80000 |
| Serratia marcescens | 24200 |
|  | 22000 |
| Shigilla paradysenteriae | 16800 |
| Spirillum rubsum | 44000 |
| Staphylococcus | 44400 |
|  | 33000 |

TABLE 3-continued

| Biological contaminant | Energy required Ergs/cm² |
|---|---|
|  | 18400 |
| *Staphylococcus aureus* | 21800 |
|  | 26000 |
|  | 49500 |
| *Streptococcus hemolyticus* | 21600 |
| *Streptococcus lactis* | 61500 |
| *Streptococcus viridans* | 20000 |

The differences in sensitivity between different kinds of biological contaminants are not great, provided that the organisms are not of the spore-forming variety. It can be seen from table 3 that the spore-forming contaminants are much more resistant than non-spore forming contaminants. By way of example, *B. subtilis*, which is a spore-forming contaminant is about 5 to 10 times more resistant than *E. coli*. Furthermore, molds and yeast are considerably more resistant than bacteria, but the resistance of many viruses is comparable with that of bacteria. By degenerating DNA and nucleoprotein, the germicidal process prevents the multiplication of the contaminants.

Experiments have shown that if radiation is confined instead of being absorbed and lost, the exposure time can be cut in half for the same killing ratio. The air purifier of the present invention accomplishes this by the use of the inner reflective housing having a coefficient of reflection of at least 60% for UV-C wavelengths.

The germicidal capabilities of two different models of the air purifier on the organisms listed in table 1 are illustrated in table 4. A first model is designed for residential use and a second model is designed for high bacteria count environment such as hospitals, kindergartens, etc., i.e. it has more germicidal power. Table 4 gives the time required to sterilize the air up to 60% and 90% free of biological contaminants (based on a lethal dose of 10,000 ergs/cm²)

TABLE 4

| Treated building area | First model | | Second model | |
|---|---|---|---|---|
| (8 feet ceilings) | 60% | 90% | 60% | 90% |
| 1500 feet square | 11 hrs | 27 hrs | 5 hrs | 12 hrs |
| 3000 feet square | 21 hr | 53 hrs | 10 hr | 25 hrs |
| 6000 feet square | 43 hrs | 107 hrs | 20 hrs | 50 hrs |

As apparent from table 4, air purifiers according to the present invention are very efficient in purifying biological contaminants, even contaminants requiring a high energy level to be destroyed.

Experiments in residential houses using the first model of air purifier of table 4 have demonstrated that a biological contaminant level of 100 to 200 CFU/m³ may be kept inside when the air outside is at a level of 500 CFU/m³. Measurement of the internal biological contamination level before the installation of the air purifier according to the present invention have revealed biological contaminant levels in the range of 600 to 1000 CFU/m³.

Figure 4:
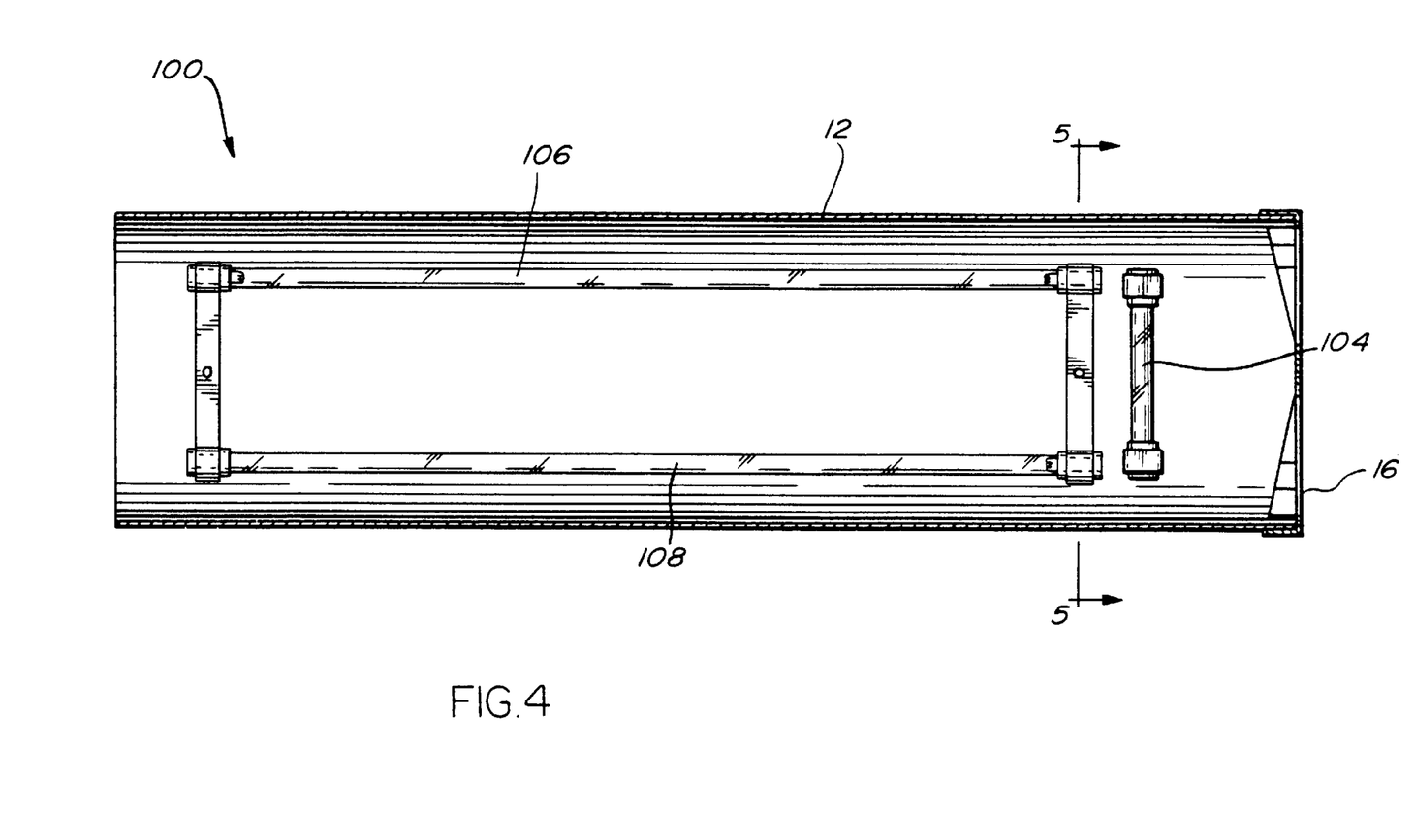
FIG. 4 is a longitudinal cross-sectional view similar to the one of FIG. 2, illustrating an air purifier according to a second embodiment of the present invention.
Figure 5:
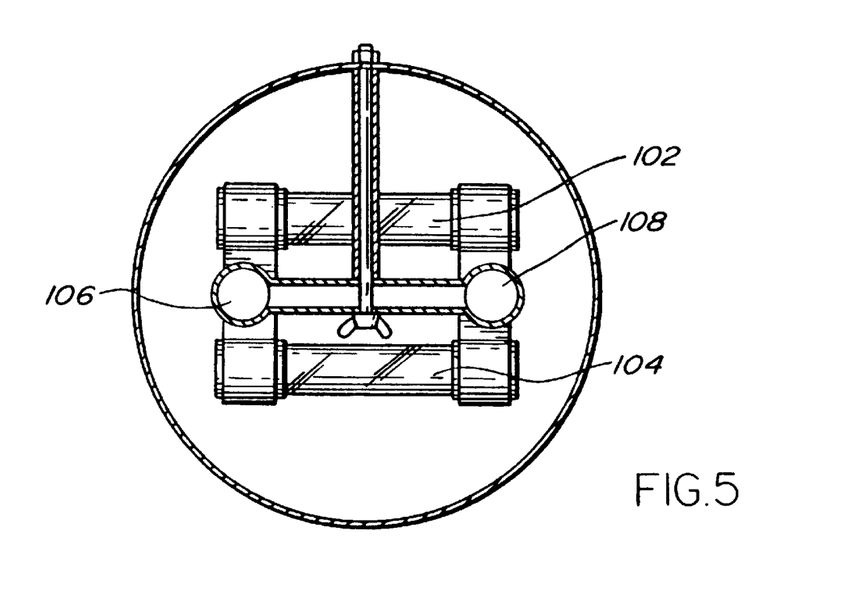
FIG. 5 is a transversal cross-sectional view taken along line 5—5 of FIG. 4.

Turning now to FIGS. 4 and 5, an air purifier 100 according to a second embodiment of the present invention will be described. The air purifier 100 is very similar to the air purifier 10 of FIGS. 1–3 with the major difference that the dual zone mercury vapor lamp tube 38 of air purifier 10 has been replaced by two UV oxidizing mercury vapor lamp tubes 102 and 104, acting as the vacuum UV source, and two UV-C germicidal mercury vapor lamp tubes 106 and 108, acting as the germicidal UV-C source.

It is to be noted that when more than one vacuum UV source are used, each vacuum UV source is in an equidistant relationship with the other vacuum UV sources and with the housing. Each vacuum UV source thereby irradiate essentially an equal volume.

As will be easily understood by one of ordianary skills in the art, an air purifier according to the present invention may be installed in an air return plenum af any existing ventilation system, air conditioning unit or heating system. More specifically, the in-duct version illustrated in the appended drawings may be installed as follows:

for residential use: In the air return plenum just before the circulation fan, before the air filter for commercial use: In the air return plenum, between the last return duct and the circulation fan.

The air purifier of the present invention may also, in some cases, be installed in the supply side of the system.

Figure 7:
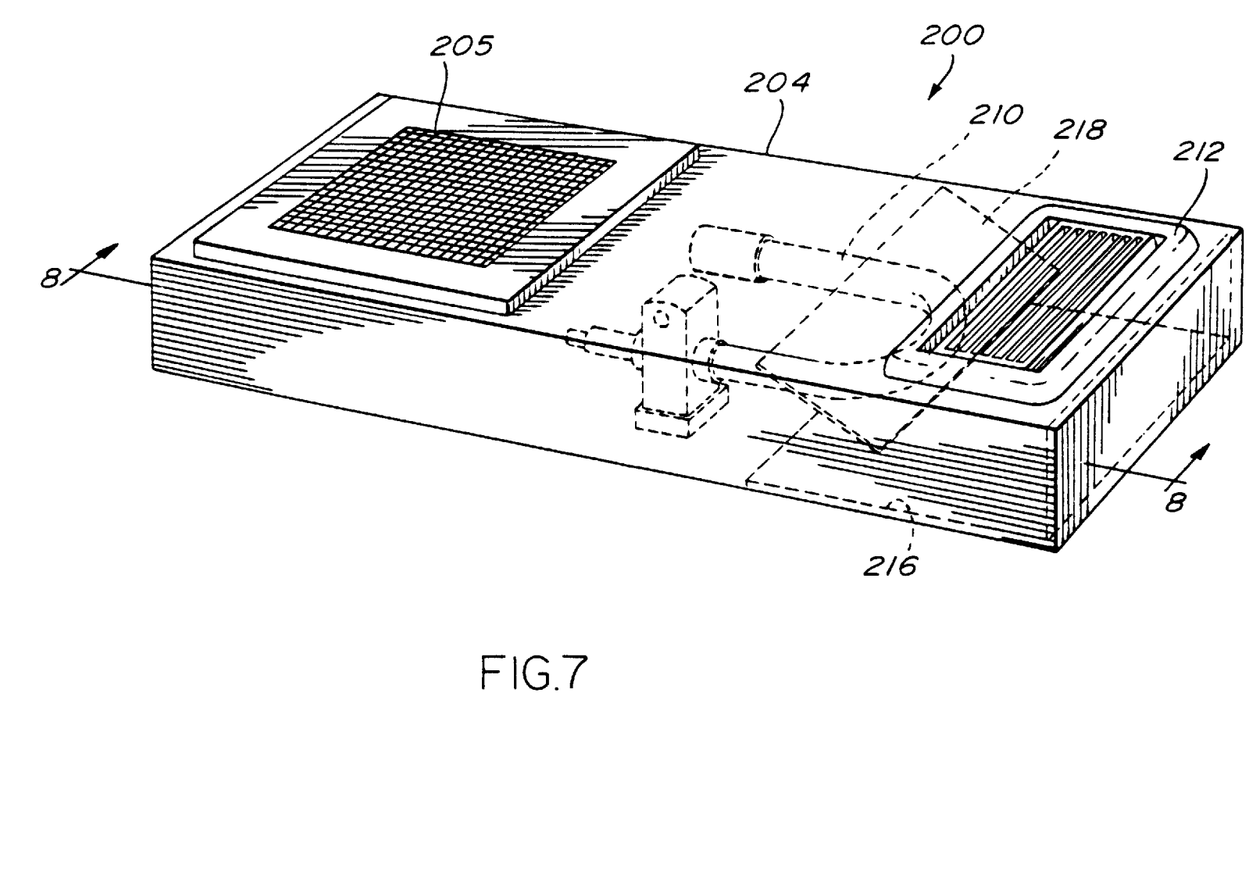
FIG. 7 is a perspective view illustrating an autonomous air purifier according to a third embodiment of the present invention.
Figure 8:
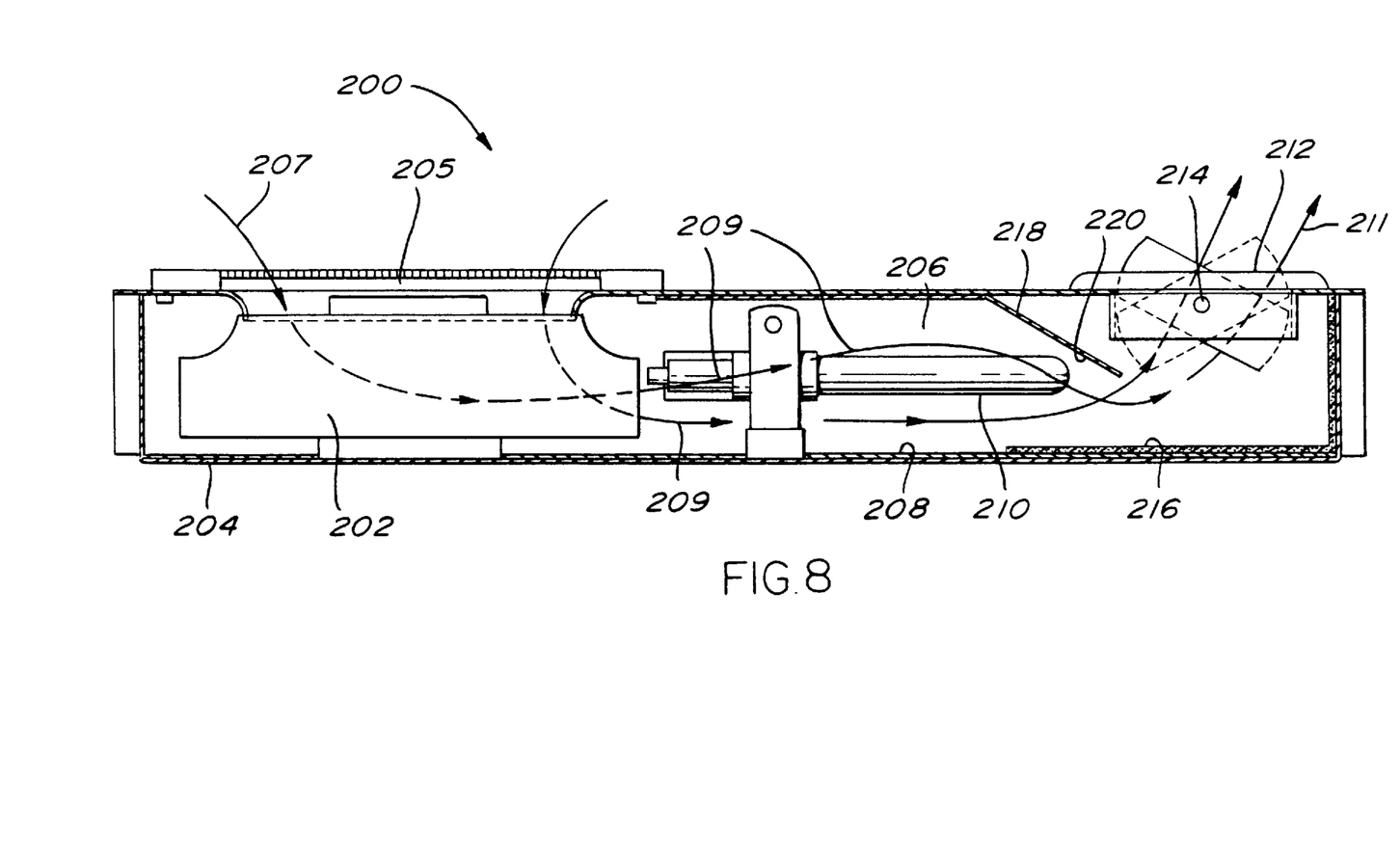
FIG. 8 is a sectional view taken along line 8—8 of FIG. 7.

Turning now to FIGS. 7 and 8 of the appended drawings, an air purifier 200 according to a third embodiment of the present invention will be described. While the air purifiers illustrated in FIGS. 1 to 6 are designed to be used in ventilation systems, the air purifier 200 is autonomous, i.e. it is provided with an electric fan to create its own air flow. The air purifier 200 may therefore be placed on a table or mounted to a wall to purify the air of a room.

As mentioned hereinabove, the air purifier 200 has a motorized fan 202 continuously drawing air in an enclosure 204 through a grating 205 (see arrow 207). The drawn air is continuously supplied to a chamber 206 (see arrows 209) having a UV reflective coating 208 as previously described with respect to air purifiers 10 and 100. A J-shaped dual zone mercury vapor lamp 210 is provided in the chamber 206 to purify the air present therein. The lamp 210 is similar to lamp 38' of FIG. 6. The air is then exhausted through a directional grating 212 having a pivot axis 214 allowing pivoting movements of the grating 212 to direct the exhausted and purified air (see arrow 211).

It is to be noted that a non-reflective coating 216 and a deflector 218 are provided in the chamber 206 to prevent UV radiations leakage. Furthermore, the inwardly facing surface 220 of the deflector 218 is provided with a UV reflective coating to increase efficiency of the lamp 210.

Optionally, the grating 205 may be removed to mount a directable conduit (not shown) to selectively draw air from a known contaminant source, for example an ashtray.

Of course, while the above description concerns preferred embodiments of the present invention, these embodiments could be modified at will without departing from the spirit and nature of the subject invention as defined in the appended claims.

What is claimed is:

1. An air purifier comprising:

a housing having an air inlet for receiving air and an air outlet for exhausting air, means for generating mono-atomic oxygen downstream of said air inlet, wherein said mono-atomic oxygen generating means being mounted within said housing, said generated mono-atomic oxygen reacts with chemical contaminants present in the air and degrades said chemical contaminants by successive oxidation to odourless and inoffensive by-products, thereby purifying air from said chemical contaminants; a portion of the mono-atomic oxygen generated combines with oxygen molecules present in the air to form residual ozone; and means for generating low frequency photons downstream of said mono-atomic oxygen generating means, said low frequency photon generating means being mounted within said housing, wherein said low frequency photons irradiate and kill biological contaminants present in the air and degrade said residual ozone produced, thereby purifying air from said biological contaminants and from residual ozone.

2. An air purifier as defined in claim 1, further comprising a turbulence generator mounted within the housing in the proximity of said air inlet and upstream from said mono-atomic oxygen generating means, wherein said turbulence generator promotes dispersion and mixing of air received within said housing through said air inlet.

3. An air purifier as defined in claim 2, wherein said turbulence generator includes a motor driven fan.

4. An air purifier as defined in claim 2, wherein said turbulence generator includes a plurality deflective baffles extending essentially perpendicular to said air inlet and oriented in such a manner as to generate turbulence in the air entering in said housing through said air inlet.

5. An air purifier as defined in claim 4, wherein the turbulence generator also includes a motor-driven fan mounted within the housing for circulating air inside said housing.

6. An air purifier as defined in claim 1, wherein said mono-atomic oxygen generating means include a vacuum ultraviolet (UV) source.

7. An air purifier as defined in claim 6, wherein said vacuum UV source includes a UV lamp tube emitting energetic UV photons.

8. An air purifier as defined in claim 7, wherein said UV lamp tube is a high intensity mercury vapor lamp emitting UV photons having a wavelength in a range of about 170 to about 220 nanometers.

9. An air purifier as defined in claim 1, wherein said low frequency photon generating means includes UV-C photons generating means.

10. An air purifier as defined in claim 9, wherein said UV-C photons generating means include a germicidal UV-C source.

11. An air purifier as defined in claim 10, wherein said germicidal UV-C source includes a UV-C lamp tube emitting photons.

12. An air purifier as defined in claim 11, wherein said UV-C lamp tube is a low intensity mercury vapor lamp emitting UV-C photons having a wavelength in a range of about 220 to about 288 nanometers.

13. An air purifier as defined in claim 6, wherein said low frequency photons generating means include a germicidal UV-C source; said vacuum UV source and said germicidal UV-C source being embodied together in a ballasted dual zone mercury vapor lamp.

14. An air purifier as defined in claim 13, wherein said ballasted dual zone mercury vapor lamp includes (a) a first upstream zone emitting UV photons having a wavelength in a range of about 170 to about 220 nanometers for purifying air from said chemical contaminants, and (b) a second downstream zone emitting UV photons having a wavelength in a range of about 220 to about 288 nanometers for purifying air from said biological contaminants and from said residual ozone.

15. An air purifier as defined in claim 14, wherein said ballasted dual zone mercury vapor lamp is generally J-shaped having a straight upstream zone and a U-shaped downstream zone integral with said upstream zone.

16. An air purifier as defined in claim 1, wherein (a) said housing has a longitudinal axis, (b) said mono-atomic oxygen generating means includes a high intensity mercury vapor lamp emitting UV photons having a wavelength in a range of about 170 to about 220 nanometers, (c) said high intensity mercury vapor lamp is essentially perpendicular to said longitudinal axis, (d) said low frequency photons generating means includes a low intensity mercury vapor lamp emitting UV photons having a wavelength in a range of about 220 to about 288 nanometers, and (e) said low intensity mercury vapor lamp is essentially parallel to said longitudinal axis.

17. An air purifier as defined in claim 1, wherein (a) said housing has a longitudinal axis, (b) said mono-atomic oxygen generating means includes at least two high intensity mercury vapor lamps emitting UV photons having a wavelength in a range of about 170 to about 220 nanometers, (c) said at least two high intensity mercury vapor lamps are positioned in substantially equidistant relationship with respect to one another and to the housing, (d) said at least two high intensity mercury vapor lamps are positioned essentially perpendicular to said longitudinal axis, (e) said low frequency photons generating means include at least two low intensity mercury vapor lamps emitting UV photons having a wavelength in a range of about 220 to about 288 nanometers, (f) said at least two low intensity mercury vapor lamps are positioned in substantially equidistant relationship with respect to one another and to the housing, and (g) said at least two low intensity mercury vapor lamps are positioned essentially parallel to said longitudinal axis.

18. An air purifier as defined in claim 1, wherein said housing has an inner reflective surface to reflect back photons emitted from said low frequency photons generating means, thereby increasing the germicidal effectiveness of said low frequency photons generating means by increasing the exposure of the biological contaminants to low frequency photons.

19. An air purifier as defined in claim 18, wherein said inner reflective surface includes aluminum.

20. An air purifier as defined in claim 1, further comprising a sensor for detecting air circulation in the vicinity of said housing and selectively energizing said mono-atomic oxygen generating means and said low frequency photons generating means upon detection of air circulation in said housing.

21. An air purifier comprising:
   a housing having a longitudinal axis, an air inlet for receiving air and an air outlet for exhausting air;
   air flow producing means for producing a flow of air in said housing from said air inlet to said air outlet, said air flow producing means promotes dispersion and mixing of air received within said housing through said air inlet;
   a high intensity mercury vapor lamp emitting UV photons having a wavelength in a range of about 170 to about 220 nanometers; said high intensity mercury vapor lamp is mounted within the housing; wherein said emitted UV photons react with oxygen molecules present in the air supplied in the housing to generate mono-atomic oxygen; the generated mono-atomic oxygen reacts, in turn, with chemical contaminants present in the air and degrades said chemical contaminants by successive oxidation to odourless and inoffensive by-products, thereby purifying air from said chemical contaminants; a portion of the mono-atomic oxygen generated combines with oxygen molecules present in the air to form residual ozone; and
   a low intensity mercury vapor lamp emitting UV-C photons having a wavelength in a range of about 220 to about 288 nanometers; said low frequency mercury vapor lamp is mounted within the housing downstream of said high intensity mercury vapor lamp, wherein said UV-C photons irradiate and kill biological contaminants present in the air and degrade said residual ozone produced, thereby purifying air from said biological contaminants and from residual ozone;

wherein (a) said housing has an inner reflective surface to reflect back UV-C photons emitted by said low intensity mercury vapor lamp, thereby increasing the germicidal effectiveness of said UV-C photons generating means by increasing the exposure of the biological contaminants to UV-C photons and (b) said high intensity mercury vapor lamp and said low intensity mercury vapor lamp are embodied together in a ballasted dual zone mercury vapor lamp.

22. An air purifier as defined in claim 21, wherein said air flow producing means include an electric fan mounted within said housing.

23. An air purifier as defined in claim 22, wherein said electric fan is mounted upstream from said high intensity mercury vapor lamp.

24. An air purifier as defined in claim 21, wherein said ballasted dual zone mercury vapor lamp is generally J-shaped.

25. An air purifier as defined in claim 21, further comprising means for preventing UV-C radiation leakage through said air outlet.

26. An air purifier comprising:

a housing having a longitudinal axis, an air inlet for receiving air and an air outlet for exhausting air;

a turbulence generator mounted within the housing in the proximity of said air inlet, said turbulence generator promotes dispersion and mixing of air received within said housing through said air inlet; said turbulence generator includes a plurality deflective baffles extending essentially perpendicular to the inlet and oriented in such a manner as to generate turbulence in the air entering in said housing through said air inlet;

a high intensity mercury vapor lamp emitting UV photons having a wavelength in a range of about 170 to about 220 nanometers; said high intensity mercury vapor lamp is mounted within the housing downstream of said turbulence generator, wherein said emitted UV photons react with oxygen molecules present in the air supplied in the housing for generating mono-atomic oxygen; the generated mono-atomic oxygen reacts, in turn, with chemical contaminants present in the air and degrades said chemical contaminants by successive oxidation to odourless and inoffensive by-products, thereby purifying air from said chemical contaminants; a portion of the mono-atomic oxygen generated combines with oxygen molecules present in the air to form residual ozone; and a low intensity mercury vapor lamp emitting UV-C photons having a wavelength in a range of about 220 to about 288 nanometers; said low frequency mercury vapor lamp is mounted within the housing downstream of said high intensity mercury vapor lamp, wherein said UV-C photons irradiate and kill biological contaminants present in the air and degrade said residual ozone produced, thereby purifying air from said biological contaminants and from residual ozone;

wherein (a) said housing has an inner reflective surface to reflect back UV-C photons emitted by said low intensity mercury vapor lamp, thereby increasing the germicidal effectiveness of said UV-C photons generating means by increasing the exposure of the biological contaminants to UV-C photons and (b) said high intensity mercury vapor lamp and said low intensity mercury vapor lamp are embodied together in a ballasted dual zone mercury vapor lamp.

27. An air purifier as defined in claim 26, wherein said ballasted dual zone mercury vapor lamp is generally J-shaped having a straight high intensity upstream zone and a U-shaped low intensity downstream zone integral with said high intensity upstream zone.

* * * * *